(12) United States Patent
Rao (10) Patent No.: US 8,718,994 B2
(45) Date of Patent: May 6, 2014

(54) LIGANDS FOR THE GLP-1 RECEPTOR AND METHODS FOR DISCOVERY THEREOF

(75) Inventor: Mohan Rao, Greensboro, NC (US)

(73) Assignee: TransTech Pharma, LLC, High Point, NC (US)

( * ) Notice: Subject to any disclaimer, the term of this patent is extended or adjusted under 35 U.S.C. 154(b) by 498 days.

(21) Appl. No.: 12/936,434

(22) PCT Filed: Apr. 8, 2009

(86) PCT No.: PCT/US2009/039905
§ 371 (c)(1),
(2), (4) Date: Oct. 5, 2010

(87) PCT Pub. No.: WO2009/126709
PCT Pub. Date: Oct. 15, 2009

(65) Prior Publication Data
US 2011/0028335 A1    Feb. 3, 2011

Related U.S. Application Data

(60) Provisional application No. 61/043,574, filed on Apr. 9, 2008.

(51) Int. Cl.
*G06G 7/58*    (2006.01)
(52) U.S. Cl.
USPC .......................................................... 703/11

(58) Field of Classification Search
USPC .......................................................... 703/11
See application file for complete search history.

(56) References Cited

U.S. PATENT DOCUMENTS

| 6,051,689 A | 4/2000 | Thorens |
| 2003/0148421 A1 | 8/2003 | Newgard et al. |
| 2006/0275288 A1 | 12/2006 | Grihalde et al. |

FOREIGN PATENT DOCUMENTS

WO    WO 2011/156655    12/2011

OTHER PUBLICATIONS

Runge et al., "Crystal Structure of the Ligand-Bound Glucagon-Like Peptide-1 Receptor Extracellular Domain" J. Biol. Chem., vol. 283(17), pp. 11340-11347 (2008).
International Search Report, PCT App. No. PCT/US09/39905, dated Jul. 23, 2009.
International Preliminary Report on Patentability, PCT App. No. PCT/US09/39905, dated Oct. 21, 2010.

*Primary Examiner* — Jerry Lin
(74) *Attorney, Agent, or Firm* — Samuel B. Rollins (57) ABSTRACT

Disclosed is the three-dimensional (3-D) structure of the GLP-1 receptor (GLP-1R) and methods by which the structure may be used to develop compounds that bind to, and/or modulate the GLP-1R. The technology described herein may be applied to the development of compounds that target the GLP-1R, or may be used to develop target compound that may bind to, and/or modulate the activity of the GLP-1R.

6 Claims, 6 Drawing Sheets

LIGANDS FOR THE GLP-1 RECEPTOR AND METHODS FOR DISCOVERY THEREOF

CROSS-REFERENCE TO RELATED APPLICATIONS

This application is a 35 U.S.C. § 371 national stage application of International Patent Application PCT/US2009/039905 (published as WO 2009/126709 A1), filed Apr. 8, 2009, which claims priority to U.S. Provisional Patent Application No. 61/043,574, filed Apr. 9, 2008.

FIELD OF INVENTION

The present invention relates to compounds that modulate the human GLP-1 receptor (GLP-1R). More particularly, the present invention comprises methods that use structural coordinates that define the three-dimensional (3-D) structure of the GLP-1R to develop compounds that modulate GLP-1R activity.

BACKGROUND

Glucagon-like peptide-1 (GLP-1) is a member of the incretin family of neuroendocrine peptide hormones secreted from the L-cells of the intestine in response to food ingestion. GLP-1 has multiple metabolic effects that are attractive for an antidiabetic agent. A key function of GLP-1 is to activate its receptor, GLP-1R, on pancreatic beta-cells to enhance glucose-dependent insulin secretion. Positive metabolic benefits of GLP-1 may include, but are not limited to, suppression of excessive glucagon production, decreased food intake, delayed gastric emptying, and improvement of b-cell mass and function. The positive effects of GLP-1 on beta-cell mass and function offers the hope that GLP-1-based therapies may delay early stage disease progression. In addition, a GLP-1 agonist could be useful in combination therapies such as with insulin in patients with type I diabetes. Unfortunately, the rapid proteolysis of GLP-1 into an inactive metabolite limits its use as a therapeutic agent.

Validation of GLP-1R agonists as a therapeutic modality was achieved by Exendin-4 (Byetta® (Amylin Pharmaceuticals, Inc.)), a peptide GLP-1 receptor agonist recently approved for the treatment of Type II diabetes mellitus. Dosing of Exendin-4 by subcutaneous administration lowers blood glucose and decreases HbA1c levels, which are important biomarker measurements for disease control. Therefore, an oral GLP-1 receptor agonist should provide glycemic control while offering the convenience of oral dosing.

GLP-1R belongs to the class B receptor sub-class of the G protein-coupled receptor (GPCR) superfamily that regulates many important physiological and pathophysiological processes. In addition to the seven transmembrane domains characteristic of all GPCR family members, class B GPCRs contain a relatively large N-terminal domain. It is believed that the binding and activation of these receptors by relatively large natural peptide ligands require both the N-terminal domain and the transmembrane domain of the receptor. As such, the identification of low molecular weight non-peptide agonist molecules for class B GPCRs has proven particularly difficult.

Further, because peptides, such as GLP-1, may lack sufficient oral bioavailability for consideration as oral drug agents, small molecule modulators of GLP-1R with oral bioavailability are highly desired. The present invention describes a class of tetrahydroisoquinoline derivatives that modulate GLP-1R.

SUMMARY

Embodiments of the present invention provide modulators for GLP-1R. The present invention may be embodied in a variety of ways.

In one embodiment, the invention may comprise a method for identifying a compound that has the ability to modulate the GLP-1R. The method may comprise the step of generating a three-dimensional model of the GLP-1R, or a portion thereof. The method may further comprise generating a three-dimensional model of a potential modulator compound of interest. Next, the method may comprise determining the nature of at least one of the atomic interactions between the potential modulator compound and the GLP-1R, or a portion thereof, as defined by the three-dimensional models for the potential modulator compound and the GLP-1R or a portion thereof.

The present invention also provides a method of generating a three-dimensional model of a protein, or a portion thereof. The method may comprise the steps of providing an amino acid sequence of the protein of interest, and comparing the amino acid sequence of the protein of interest to the amino acid sequence of other proteins for which a three-dimensional structure has been defined to identify a second protein having a predetermined level of sequence identity to the protein of interest. Once a second protein having a known 3-D structure has been identified, the method may further include the step of aligning conserved residues from the protein of interest with conserved residues from the second protein. Next, the sequence for the protein of interest may be threaded along the three-dimensional structure of the second protein, such that the position of at least two conserved residues from both proteins are aligned.

The present invention also comprises a computer model for the GLP-1R or a portion thereof, comprising structural coordinates for a three-dimensional model for the GLP-1R, or a portion thereof, visualized on a computer screen.

The present invention also provides compounds that modulate the GLP-1R. In one embodiment, the compounds may be useful in the treatment of a disease state responsive to the modulation of the GLP-1R. The compound may comprise a pharmacophore. For example, in one embodiment, the present invention may comprise a pharmacophore comprising at least one atom or molecular group that interacts with at least one atom or molecular group of the GLP-1R, or a portion thereof. In one embodiment, the compound interacts with the GLP-1R, or a portion thereof, to modulate the activity of the GLP-1R. For example, the compound may be a compound identified by docking a computer representation of the compound, or a synthetic variant thereof, with a computer representation of a three-dimensional structure of the GLP-1R, or a portion thereof. In yet another embodiment, the present invention may comprise a pharmaceutical composition. For example, the present invention may comprise a pharmaceutical composition comprising a compound identified by docking a computer representation of the compound with a computer representation of a structure of the GLP-1R, or a portion thereof.

The present invention also comprises a method of conducting a drug-discovery business. The method may comprise the step of generating a three-dimensional structural model of a target molecule of interest on a computer. Also, the method may comprise generating a three-dimensional structural model of a potential modulator compound of the target molecule on a computer, and docking the model for the potential modulator compound with a 3-D structural model of the target molecule so as to minimize the free energy of the interaction between the target molecule and the potential modulator. In this way, a modulator compound that may interact with the target may be identified. The method may also include the subsequent steps of providing a modified structure for the modulator compound of interest, and assessing whether the modified structure has a lower free energy of interaction with the target than the original modulator compound.

Figure 2A:
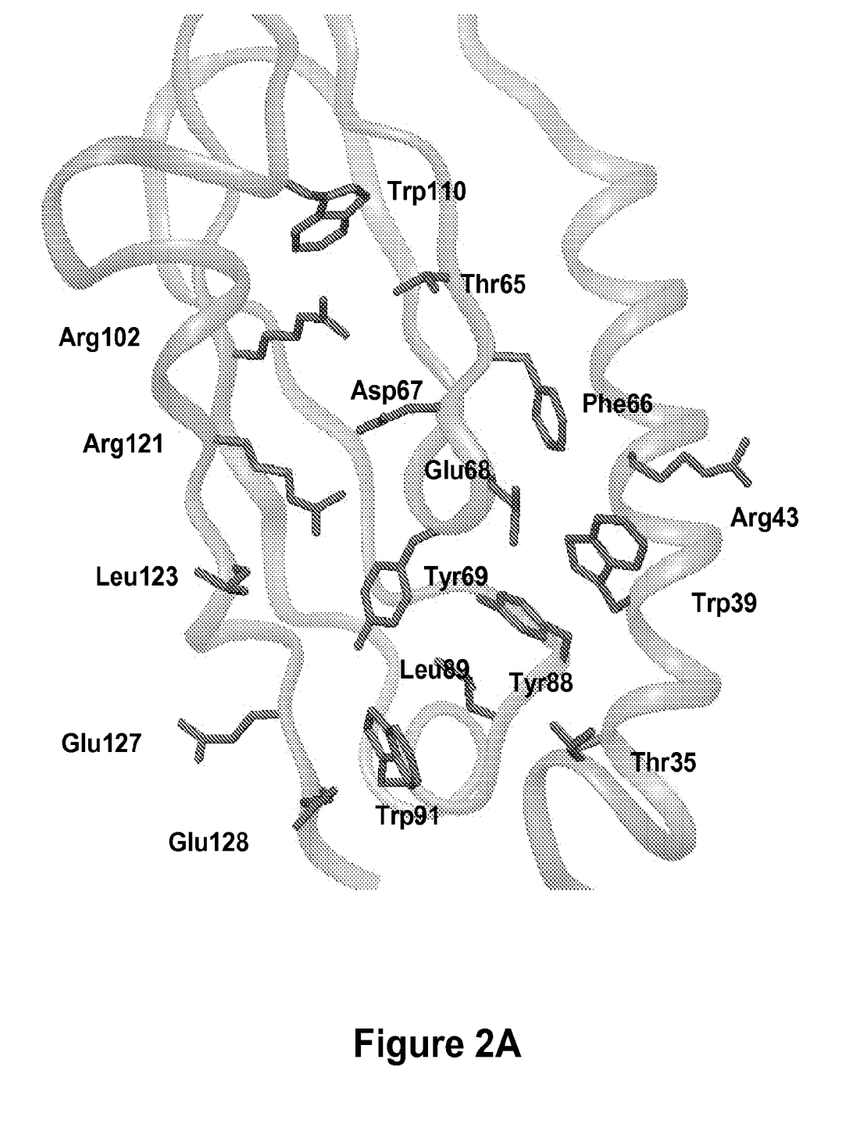
FIGS. 2A and 2B show three-dimensional homology threading models of the GLP-1R generated using methods in accordance with the present invention. The models depict two putative binding sites on the extracellular portion of the GLP-1R: Site 1 and Site 2, respectively.
Figure 2B:
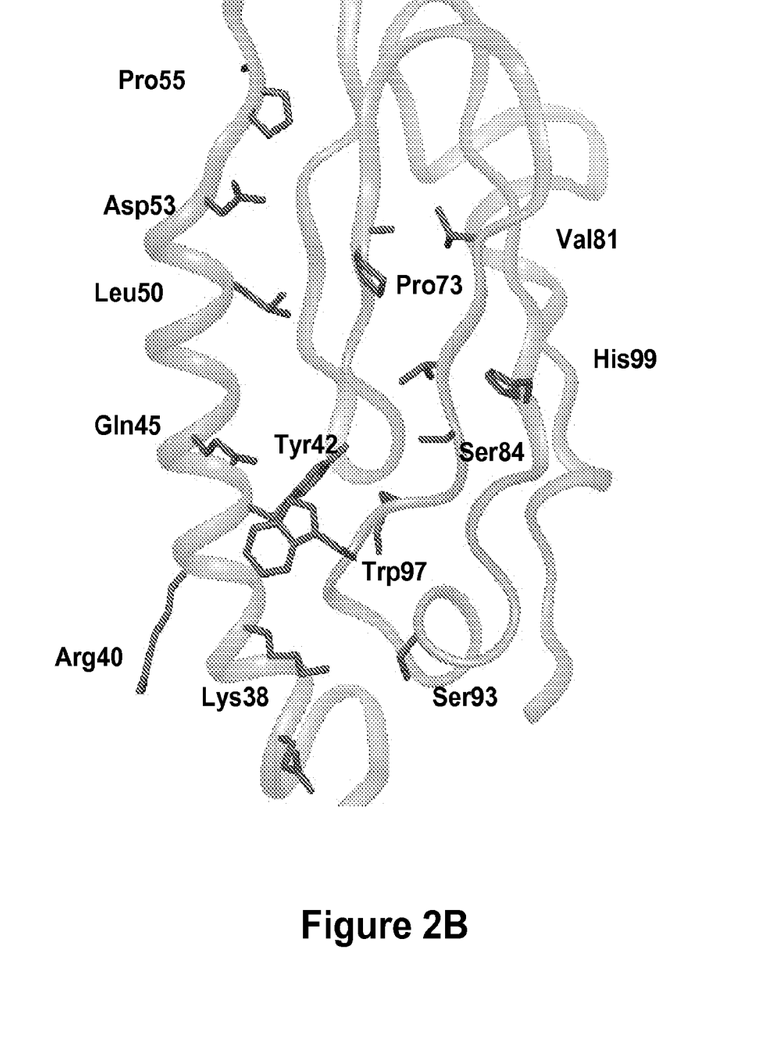

The present invention comprises methods that use structural coordinates that define the three-dimensional (3-D) structure of the GLP-1R to develop compounds that modulate GLP-1R activity. In one aspect of the present invention, structural models for human, mouse, rat, pig, chicken, chimpanzee and dog GLP-1 receptor sequences are disclosed. In another aspect of the present invention, a structural model is disclosed for the ligand binding domain of the GLP-1R, a synthetic mimic of the GLP-1R and allosteric binding modulators of the GLP-1R are disclosed. In another aspect of the present invention, a method is disclosed for identifying a potential modulators (allosteric and orthosteric) for human, mouse, rat, pig and dog GLP-1R by determining binding interactions between a test compound and atomic contacts of ligand binding domain residues of the GLP-1R is disclosed. This method may comprise generating a atomic contacts using computational modeling tools; and generating test compounds with a spatial structure as shown in FIGS. 2A and 2B. In yet another aspect of the present invention, a method is disclosed for identifying a potential modulator of the GLP-1R function by docking a computer representation of a test compound with a computer representation of a structure of human, mouse, chicken, rat, pig and dog GLP-1R, or ligand binding domain thereof, as shown in FIGS. 2A, 2B, 3A and 3B. In still a further aspect of the present invention, a method is disclosed for identifying modulators of the GLP-1R function by binding a test compound with any of the residues of the GLP-1R shown in FIGS. 2A and 2B. In another aspect of the present invention, a method is disclosed for the design of ligands for human, mouse, rat, pig, dog GLP-1R based on the three-dimensional structure of ligand binding domains as shown in FIGS. 2A and 2B. In a further aspect of the present invention, a method is disclosed for the design of antagonist and agonists for Sites 1 and 2, as shown in FIGS. 2A and 2b.

In another embodiment, the present invention comprises treatment of a disease state responsive to the modulation of the GLP-1R using compounds identified by the methods and systems of the present invention. The disease state may include disorders wherein activation of the GLP-1R is beneficial, including metabolic disorders, wherein activation of the GLP-1R is beneficial; glucose intolerance; hyperglycaemia; dyslipidemia; Type 1 diabetes; Type 2 diabetes; hypertriglyceridemia; syndrome X; insulin resistance; IGT; obesity; diabetes as a consequence of obesity; diabetic dyslipidemia; hyperlipidemia; cardiovascular diseases; hypertension, and complications resulting from or associated with diabetes including but not limited to neuropathy, retinopathy, nephropathy, impaired wound healing, and the like, or any other indications listed in US Patent Publication No. 2004/0127423A3 or U.S. Pat. No. 6,927,214, the content of which is herein incorporated by reference.

There may be advantages provided by certain embodiments of the present invention. For example, the methods of the present invention may provide a means to identify a plurality of putative pharmacological agents based upon the known 3-D structure of a target protein. Also, the present invention may provide a means to modify the structure of a putative pharmacological agent in silico to determine how such changes can effect the activity of the agent. Making such determinations in silico provides the ability to rapidly evaluate a large number of compounds. Also, making such determinations in silico allows for a rational approach to drug development, such that compounds may be systematically developed and their activity evaluated.

There are, of course, additional features of the invention, which will be described in more detail hereinafter. It is to be understood that the invention is not limited in its application to the specific details as set forth in the following description and figures. The invention is capable of other embodiments and of being practiced or carried out in various ways.

DETAILED DESCRIPTION

Definitions

The following definitions may be used to understand the description herein. Unless defined otherwise, all technical and scientific terms used herein have the same meaning as commonly understood by one of ordinary skill in the art. Practitioners are particularly directed to Current Protocols in Molecular Biology (Ansubel) for definitions and terms of the art. Abbreviations for amino acid residues are the standard 3-letter and/or 1-letter codes used in the art to refer to one of the 20 common L-amino acids.

A GLP-1R or part thereof in the present invention may be a wild type protein or part thereof, a mutant protein or part thereof, or variant or homologue of such a protein. As used herein, the term "wild type" refers to a polypeptide having a primary amino acid sequence which is identical with the native polypeptide. The term "mutant" refers to a polypeptide having a primary amino acid sequence which differs from the wild type sequence by one or more amino acid additions, substitutions or deletions. A mutant may or may not be functional. As used herein, the term "variant" refers to a naturally occurring polypeptide which differs from a wild-type sequence. As used herein, when referring to a protein, the terms "portion" or "part" indicate that the polypeptide comprises a fraction (or fractions) of the amino acid sequence referred to.

"Polypeptide" and "protein" are used interchangeably herein to describe protein molecules that may comprise either partial or full-length proteins.

As used herein, "small organic molecules" are molecules of molecular weight less than 2,000 Daltons that contain at least one carbon atom.

The term "vector" refers to a nucleic acid molecule that may be used to transport a second nucleic acid molecule into a cell. In one embodiment, the vector allows for replication of DNA sequences inserted into the vector. The vector may comprise a promoter to enhance expression of the nucleic acid molecule in at least some host cells. Vectors may replicate autonomously (extra chromosomal) or may be integrated into a host cell chromosome. In one embodiment, the vector may comprise an expression vector capable of producing a protein derived from at least part of a nucleic acid sequence inserted into the vector.

As used herein, the term "interact" refers to a condition of proximity between a ligand or compound, or portions or fragments thereof, and a portion of a second molecule of interest. The interaction may be non-covalent, for example, as a result of hydrogen-bonding, van der Waals interactions, or electrostatic or hydrophobic interactions, or it may be covalent.

As used herein, the term "atomic contacts" or "atomic interaction" refers to the inter-atomic contact between atoms in a test compound and atoms in a second molecule (e.g., the protein of interest) for which a three-dimensional model is made. The atomic interaction is governed by geometric and physiochemical complementarity as well as steric fit between the two molecules for which the atomic contacts/interaction is evaluated. For example, potential atomic interactions between the GLP-1R ligand binding domain and sample small molecules are described, at least in part, by FIGS. 3a and 3b.

As used herein, the term "docking" refers to a process by which a test compound is placed in close proximity with a second molecule (e.g., the protein of interest). Docking is also used to describe the process of finding low energy conformations of a test compound and a second molecule (e.g., the protein or polypeptide of interest, or portion thereof). Docking studies include molecular modeling studies aimed at finding a proper fit between a ligand and its binding site.

As used herein, the term "docked" refers to a favorable configuration of a test compound positioned within a given site on a molecule of interest.

As used herein, the term "hang point residues" refers to residues on a first molecule of known structure that are then used as anchors for the threading of a second molecule of unknown structure along the structure of the first molecule so as to determine a structure for the second molecule.

As used herein, the term "conserved residues" refers to amino acids that are the same among a plurality of proteins having the same structure and/or function. A region of conserved residues may be important for protein structure or function. Thus, contiguous conserved residues as identified in a three-dimensional protein may be important for protein structure or function. To find conserved residues, or conserved regions of 3-D structure, a comparison amino acid sequence for the same or similar proteins from different species, or of individuals of the same species, may be made.

As used herein, the term "homologue" means a polypeptide having a degree of homology with the wild-type amino acid sequence. Homology comparisons can be conducted by eye, or more usually, with the aid of readily available sequence comparison programs. These commercially available computer programs can calculate percent homology between two or more sequences (e.g. Wilbur, W. J. and Lipman, D. J., 1983, *Proc. Natl. Acad. Sci. USA,* 80:726-730). For example, homologous sequences may be taken to include an amino acid sequences which in alternate embodiments are at least 75% identical, 85% identical, 90% identical, 95% identical, or 98% identical to each other.

The terms "identity" or "percent identical" refers to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, 1981, *Adv. Appl. Math.* 2:482; Needleman and Wunsch, 1970, *J. Mol. Biol.* 48:443; Pearson and Lipman, 1988, *Proc. Natl. Acad. Sci., USA,* 85:2444) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. In one embodiment, the percent identity of two sequences may be determined using GCG with a gap weight of 1, such that each amino acid gap is weighted as if it were a single amino acid mismatch between the two sequences.

As used herein, a polypeptide or protein "domain" comprises a region along a polypeptide or protein that comprises an independent unit. Domains may be defined in terms of structure, sequence and/or biological activity. In one embodiment, a polypeptide domain may comprise a region of a protein that folds in a manner that is substantially independent from the rest of the protein. Domains may be identified using domain databases such as, but not limited to, PFAM, PRODOM, PROSITE, BLOCKS, PRINTS, SBASE, ISREC PROFILES, SAMRT, and PROCLASS.

As used herein, "ligand binding domain" (LBD) refers to a domain of a protein responsible for binding a ligand. The term "ligand binding domain" includes homologues of a ligand binding domain or portions thereof. In this regard, deliberate amino acid substitutions may be made in the LBD on the basis of similarity in polarity, charge, solubility, hydrophobicity, hydrophilicity, and/or the amphipathic nature of the residues, as long as the binding specificity of the ligand binding domain is retained.

As used herein, the "ligand binding site" comprises residues in a protein that directly interact with a ligand, or residues involved in positioning the ligand in close proximity to those residues that directly interact with the ligand. The interaction of residues in the ligand binding site may be defined by the spatial proximity of the residues to a ligand in the model or structure. The term "ligand binding site" includes homologues of a ligand binding site or portions thereof. In this regard, deliberate amino acid substitutions may be made in the ligand binding site on the basis of similarity in polarity, charge, solubility, hydrophobicity, hydrophilicity, and/or the amphipathic nature of the residues, as long as the binding specificity of the ligand binding site is retained. For I7L, the ligand binding site may be defined as comprising those residues described below for each of Site 1 and Site 2. In another embodiment, the ligand binding site may be defined as comprising those residues as described below for each of Site 1 and Site 2 and any other residues that are within a 3 angstrom radius thereof.

As used herein, a "ligand" refers to a molecule or compound or entity that associates with a ligand binding domain, including substrates or analogues or parts thereof. As described herein, the term "ligand" may refer to compounds that bind to the protein of interest. A ligand may be a modulator. Or, a ligand may not have a biological effect. Or, a ligand may block the binding of other ligands thereby inhibiting a biological effect. Ligands may include, but are not limited to, small molecule inhibitors of the activity of protein. These small molecules may include peptides, peptidomimetics, organic compounds and the like.

As used herein, a "modulator compound" refers to a molecule which changes or alters the biological activity of a molecule of interest. A modulator compound may increase or decrease activity, or change the physical or chemical characteristics, or functional or immunological properties, of the molecule of interest. A modulator compound may include natural and/or chemically synthesized or artificial peptides, modified peptides (e.g., phosphopeptides), antibodies, carbohydrates, monosaccharides, oligosaccharides, polysaccharides, glycolipids, heterocyclic compounds, nucleosides or nucleotides or parts thereof, and small organic or inorganic molecules. A modulator compound may be an endogenous physiological compound or it may be a natural or synthetic compound. Or, the modulator compound may be a small organic molecule. The term "modulator compound" also includes a chemically modified ligand or compound, and includes isomers and racemic forms.

The terms "structural coordinates" or "atomic coordinates" as used herein refers to a set of values that define the position of one or more amino acid residues or molecules with reference to a system of axes. A data set of structural coordinates defines the three dimensional structure of a molecule or molecules. Structural coordinates can be slightly modified and still render nearly identical three dimensional structures. A measure of a unique set of structural coordinates is the root-mean-square deviation of the resulting structure. In alternate embodiments, structural coordinates that render three dimensional structures that deviate from one another by a root-mean-square deviation of less than 3 angstroms, or less than 2.0 angstroms, or less than 0.5 angstroms, or less than 0.3 angstroms, may be viewed by a person of ordinary skill in the art as identical. Variations in structural coordinates may be generated because of mathematical manipulations of the structural coordinates of the GLP-1R. Variations in structure due to mutations, additions, substitutions, and/or deletions of the amino acids, or other changes in any of the components that make up a structure of the invention may also account for modifications in structural coordinates. If such modifications are within the standard error as compared to the original structural coordinates, the resulting structure may be considered to be the same or equivalent. Therefore, a ligand that bound to a ligand binding domain of a GLP-1R would also be expected to bind to another ligand binding domain whose structural coordinates defined a shape that fell within the margin of error defined by the first structure. Such modified structures of a ligand binding domain are also within the scope of the invention.

As used herein, a structural "model" of a protein of interest, a polypeptide of interest, or any other compound of interest, may be in two or three dimensions. For example, a computer model may be in three dimensions despite the constraints imposed by a computer screen, if it is possible to scroll along at least a pair of axes, causing rotation of the image. Also, a model of a protein or chemical compound of interest may be defined by the structural coordinates for the protein or compound of interest.

As used herein, the terms "modeling" or "generating a model" includes the quantitative and qualitative analysis of molecular structure and/or function based on atomic structural information and interaction models. The term may include conventional numeric-based molecular dynamic and energy minimization models, interactive computer graphic models, modified molecular mechanics models, distance geometry, and other structure-based constraint models.

The term "peptide mimetics" are structures which serve as substitutes for peptides in interactions between molecules (Morgan et al., 1989, *Ann. Reports Med. Chem.*, 24:243-252). Peptide mimetics may include synthetic structures that may or may not contain amino acids and/or peptide bonds but that retain the structural and functional features of a peptide, or agonist, or antagonist. Peptide mimetics also include peptoids, oligopeptoids (Simon et al., 1972, *Proc. Natl. Acad, Sci., USA,* 89:9367); and peptide libraries containing peptides of a designed length representing all possible sequences of amino acids corresponding to a peptide, or agonist or antagonist of the invention.

As used herein, "pharmacophore" is a collection of steric and electronic features that are necessary to ensure the optimal supramolecular interactions with a specific biological target structure. A pharmacophore may comprise a structural definition that comprises a set of active molecules. A pharmacophore may comprise a modulator compound.

As used herein, an "effective amount" as used herein means the amount of an agent that is effective for producing a desired effect in a subject. The term "therapeutically effective amount" denotes that amount of a drug or pharmaceutical agent that will elicit the therapeutic response of an animal or human that is being sought. The actual dose which comprises the effective amount may depend upon the route of administration, the size and health of the subject, the disorder being treated, and the like.

The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The term "a" or "an" as used herein may refer to more than one object unless the context clearly indicates otherwise. The term "or" is used interchangeably with the term "and/or" unless the context clearly indicates otherwise.

Embodiments of the present invention provide a method for identifying a compound having the ability to modulate the GLP-1R. The method may comprise the steps of: (a) generating a three-dimensional model of a the GLP-1R, or a portion thereof; (b) generating a three-dimensional model of a potential modulator compound of interest; and (c) determining at least one atomic interaction between the potential modulator compound and the GLP-1R, or a portion thereof, as defined by the three-dimensional models of each.

The method may be performed using a computer. Thus, in one embodiment, the method comprises the steps of: (a) generating a three-dimensional computer model of the GLP-1R, or a portion thereof; (b) generating a three-dimensional computer model of the potential modulator compound of interest; (c1) using a computer to dock the three-dimensional model of the potential modulator compound within the model of the GLP-1R or a portion thereof; and (c2) quantifying at least one atomic interaction between the potential modulator compound and the GLP-1R, or a portion thereof.

The method further allows for varying the structure of the potential modulator compound to determine how changes to the structure of the modulator may affect the fit of the compound with the protein of interest, such as GLP-1R. Thus, the method may further comprise the steps of modifying the computer model of the potential modulator compound, and evaluating how modifying the computer model of the potential modulator compound changes at least one atomic interaction between of the model of the potential modulator compound and the model of the GLP-1R, or portion thereof. The potential modulator compound may be modified in silico. Thus, in one embodiment, the step of modifying the computer model of the potential modulator compound of interest comprises the step of searching a library of molecular structures for molecular fragments that can be linked to the potential modulator compound, wherein a molecular fragment comprises at least one atom. The method may further comprise linking a molecular fragment to the potential modulator compound to generate a modified compound. The modified compound may then be evaluated by docking the modified compound to the GLP-1R and quantifying at least one atomic interaction between the modified compound and the GLP-1R.

It may not be required to determine the entire structure of the protein of interest to identify compounds that may act as modulators of the protein. For example, the three-dimensional model of the GLP-1R may comprise only a portion of the protein. Thus, the model may comprise a ligand binding domain. Additionally or alternatively, the model may comprise a ligand binding site.

It is also not necessarily required to determine how each amino acid of the entire structure of the protein of interest interacts with a potential modulator compound to identify compounds that may act as modulators of the protein. For example, the amino acid used to determine an atomic interaction between a potential modulator compound and the GLP-1R may comprise a residue that is conserved in the GLP-1R. Additionally, and/or alternatively, an amino acid used to determine an atomic interaction between a potential modulator compound and the GLP-1R may comprise a residue that is present in, or affects the structure of, the ligand binding domain and/or the ligand binding site.

The model of the GLP-1R may comprise a variety of formats. In one embodiment, the model may comprise a three-dimensional structural model. Or, the model of the GLP-1R may comprise structural coordinates presented as the position of individual atoms of the GLP-1R, or a portion thereof, in space. For example, the model of the GLP-1R, or a portion thereof, may comprise the x, y, and z atomic coordinates.

The method may be performed using a computer. Thus, in one embodiment, the method comprises the steps of: (a) generating a three-dimensional computer model of the GLP-1R, or a portion thereof; (b) generating a three-dimensional computer model of the potential modulator compound; (c1) using a computer to dock the three-dimensional model of the potential modulator compound with the model of the GLP-1R, or a portion thereof; and (c2) quantifying at least one atomic interaction between the potential modulator compound and the GLP-1R as defined by the docking of the model of the potential modulator compound in the computer model of the GLP-1R, or a portion thereof.

The method further allows for varying the structure of the potential modulator compound to determine how changes in the structure can affect the fit of the potential modulator compound with the protein of interest. Thus, the method may further comprise the steps of modifying the computer model of the potential modulator compound, and evaluating how modifying the computer model of the potential modulator compound affects the atomic interactions between of the model of the potential modulator compound and the model of the GLP-1R, or portion thereof. The potential modulator compound may be modified in silico. Thus, in one embodiment, the step of modifying the computer model of the potential modulator compound of interest comprises the step of searching a library of molecular structures for molecular fragments that can be linked to the potential modulator compound, wherein a molecular fragment comprises at least one atom. The method may further comprise linking a molecular fragment to the potential modulator compound to generate a modified compound. The modified compound may then be evaluated by docking the modified compound to the GLP-1R, or a portion thereof, and determining the atomic interactions between the modified compound and the GLP-1R.

It is not necessarily required to determine the entire structure of the protein of interest to identify compounds that may act as modulators of the protein. For example, the three-dimensional model of the protein of interest may comprise only a portion of the protein.

It may not be required to determine how each amino acid of the entire structure of the GLP-1R interacts with a potential modulator compound to identify compounds that may act as modulators of the GLP-1R. Additionally, or alternatively, an amino acid used to determine an atomic interaction between a potential modulator compound and the GLP-1R may comprise a residue that is present in, or affects the structure of, the ligand binding domain and/or ligand binding site.

Depending on the source of the protein used to generate a three-dimensional structure of the protein of interest, such as GLP-1R, there may be some variability in the absolute positioning of each amino acid. Still, it is to be expected that the relative positions of conserved amino acids may be maintained.

The analysis may further employ a modified protein. Thus, the potential modulator compound may be evaluated for its interaction with a modified GLP-1R, or portion thereof, wherein the modified GLP-1R comprises at least one of an amino acid substitution, an amino acid deletion, or an amino acid insertion.

The nature of the interaction between the potential modulator compound and the protein of interest may be defined in terms of the atomic interaction between the compound and the protein of interest.

The present invention also comprises a method of generating a three-dimensional model of a protein of interest, or a portion thereof. In one embodiment, method may comprise the steps of: (a) providing an amino acid sequence of a protein of interest; (b) comparing the amino acid sequence of the protein of interest to the amino acid sequences of a plurality of other proteins; (c) identifying a second protein for which a three-dimensional structure has been defined, and that has a predetermined level of sequence identity to the protein of interest; (d) aligning conserved residues from the protein of interest with conserved residues from the second protein; and (e) threading the protein of interest along the three-dimensional structure of the second protein such that the position of at least two conserved residues from both proteins are aligned.

The protein aligned with the protein of interest may also comprise a protein having a similar sequence to the protein of interest. The level of sequence identity may range from at least 5% sequence identity, to more than 10% sequence identity, to more than 20% sequence identity. Also, the protein aligned with the protein of interest may comprise a protein having a similar function as the protein of interest.

The present invention may also comprise a structural model for a protein of interest, or a portion of a protein, that may be manipulated using a computer. In one example embodiment, the present invention may comprise a computer model for the GLP-1R, or a portion thereof. The model may comprise atomic coordinates for a three-dimensional model for the GLP-1R, or a portion thereof, visualized on a computer screen.

In one embodiment, the computer model of the protein of interest may comprise atomic coordinates presented as the position of individual atoms of the GLP-1R, or a portion thereof, in space.

Also, the model may comprise a three-dimensional computer model of a potential modulator compound docked into the GLP-1R structure such that the atomic interaction between the GLP-1R and the potential modulator compound may be quantified. The atomic interactions between the GLP-1R and the potential modulator compound may be defined at least in part determining atomic coordinates for the potential modulator compound as it interacts with the GLP-1R.

The model allows for varying the structure of the potential modulator compound to determine how changes in the structure of the modified compound can effect the fit of the compound with the protein of interest. Thus, the model may further comprise a three-dimensional model of a modified compound docked with the GLP-1R structure. The potential modulator compound may be modified in silico. Thus, in one embodiment, the step of modifying the computer model of the potential modulator compound of interest comprises the step of searching a library of molecular structures for molecular fragments that can be linked to the potential modulator compound, wherein a molecular fragment comprises at least one atom, and linking the fragments to the compound. The modified compound may then be evaluated by docking the modified compound to the GLP-1R, or a portion thereof, and determining the atomic interactions between the modified compound and the GLP-1R.

The present invention also comprises a pharmacophore having a structure required to modify the activity of the protein of interest. For example, the pharmacophore may comprise at least one atom or molecular group that interacts with at least one atom or molecular group of the GLP-1R, or a portion thereof. Additionally, the three dimensional structure of the pharmacophore may comprise a plurality of atoms or molecular groups that interact with at least one atom or molecular group of a three-dimensional structure of the GLP-1R, or a portion thereof To be active as a modulator of the GLP-1R, the pharmacophore may interact with the ligand binding domain of the GLP-1R, or a portion thereof, such as the ligand binding site.

The nature of the interaction between the pharmacophore and the protein of interest may be defined in terms of the atomic interaction between the pharmacophore and the protein of interest.

The pharmacophore may be defined by its ability to interact with amino acids in the protein of interest that are important for substrate binding.

The computer model may further employ a modified protein. Thus, the pharmacophore may be evaluated for its interaction with a modified GLP-1R, or portion thereof, wherein the modified GLP-1R comprises at least one of an amino acid substitution, an amino acid deletion, or an amino acid insertion.

In yet another embodiment, the present invention comprises compounds that interact with at least one atom or molecular group of the GLP-1R. In an embodiment, the compounds include molecules that interact with residues known to be in the ligand binding domain and/or ligand binding site. Examples of such compounds that may modulate the activity of GLP-1R are disclosed in commonly owned U.S. patent application Ser. No. 12/399,504, filed Mar. 6, 2009, herein incorporated by reference.

The interaction between the compound and the GLP-1R may comprise an in silico interaction defined by a computer model of the structure of the compound and a computer model of the GLP-1R, or a portion thereof. Thus, the present invention may also comprise a compound identified by docking a computer representation of the compound with a computer representation of a structure of the GLP-1R, or a portion thereof.

The nature of the interaction between the compound and the protein of interest may be defined in terms of the atomic interaction between the compound and the protein of interest.

The present invention also comprises pharmaceutical compositions comprising compounds able to modify the activity of a protein of interest. In one embodiment, the protein of interest may comprise the GLP-1R. In one embodiment, the present invention may comprise a pharmaceutical composition comprising a compound identified by docking a computer representation of the compound with a computer representation of a three-dimensional structure of the GLP-1R, or a portion thereof.

The nature of the interaction between the compound of the pharmaceutical composition and the protein of interest may be defined in terms of the atomic interaction between the compound and the protein of interest.

The pharmaceutical composition may comprise the compound present in a therapeutically effective amount. The dosage used for the pharmaceutical compositions of the present invention may vary depending on the specific compound being used, as well as the methods of administration. In one embodiment, a therapeutically effective amount may comprise a dose in a range from about 0.01 to 1,000 mg of active compound per kg body weight per day.

The present invention also comprises a method of conducting a drug-discovery business. The method may comprise the step of generating a three-dimensional structural model of a target molecule of interest on a computer. Also, the method may comprise generating a three-dimensional structural model of a potential modulator compound of the target molecule on a computer, and docking the model for the potential modulator compound with the target molecule so as to minimize the free energy of the interaction between the target molecule and the potential modulator. In this way, a modulator compound that may interact with the target may be identified. The method may also include the subsequent steps of providing a modified structure for the modulator compound of interest, and assessing whether the modified structure has a lower free energy of interaction with the target than the original structure for the modulator compound.

The method may further include evaluating at least some of the potential modulator compounds identified by in silico screening in a biological assay. Once compounds initially identified by the in silico assay are corroborated by a biological assay, animal studies may be used for detailed therapeutic profiling, and pharmaceutical compositions may then be developed. Or, additional in silico assays may be conducted on compounds that appear to be promising based on the biological data.

The compound may comprise a small organic compound.

Structural Modeling of the GLP-1R

Embodiments of the present invention comprise computer modeling methods and systems to identify and optimize specific small molecules that bind to, and thus, are able to modulate the activity of, a particular target protein. In one embodiment, the protein is the GLP-1R. Also provided by the present invention are compounds identified using the modeling methods described herein.

Thus, in one embodiment, the present invention provides a method of generating a three-dimensional model of a protein of interest, such as GLP-1R, or a portion thereof. The method may comprise the steps of providing an amino acid sequence of the protein of interest and comparing the amino acid sequence of the protein of interest to the amino acid sequences of other proteins to identify a second protein for which a three-dimensional structure has been defined, and that has a predetermined level of sequence identity to the protein of interest. Once a second protein having a known structure has been identified, the method may include the step of aligning conserved residues from the protein of interest with conserved residues from the second protein. Next, the sequence for the protein of interest may be threaded along the three-dimensional structure of the second protein such that the position of at least two conserved residues from both proteins are aligned. The conserved residues from the first protein and the second protein may comprise residues that are essential for protein function.

Thus, as a first step, a three-dimensional model of the protein of interest may be generated. To generate a three dimensional model of a protein of interest, a sequence comparison to proteins with experimentally determined three-dimensional structures may be performed. The protein aligned with the protein of interest may comprise a protein having a similar sequence to the protein of interest. The level of sequence identity may range from at least 5% sequence identity, to more than 10% sequence identity, to more than 20% sequence identity.

The protein aligned with the protein of interest may not necessarily be functionally related to the protein of interest. Or, the protein aligned with the protein of interest may comprise a protein having a similar function to the protein of interest. In this way, conserved residues that have similar functions in the two proteins may be aligned.

In one embodiment, the protein of interest may comprise the GLP-1R.

To develop a three dimensional structure for the GLP-1R, TTPredict® site search algorithms may be used to identify the ligand binding site of the GLP-1R based on the location of site residues. Also, TTPredict® algorithms may be used to identify known GLP-1R-homologous sequences using BLAST searches on protein sequence databases. TTPredict® algorithms may also be used to access a number of publicly available and vendor-supplied fold recognition programs to analyze the GLP-1R sequence folds (e.g., MSI suite of programs, TTPGene).

Figure 1:
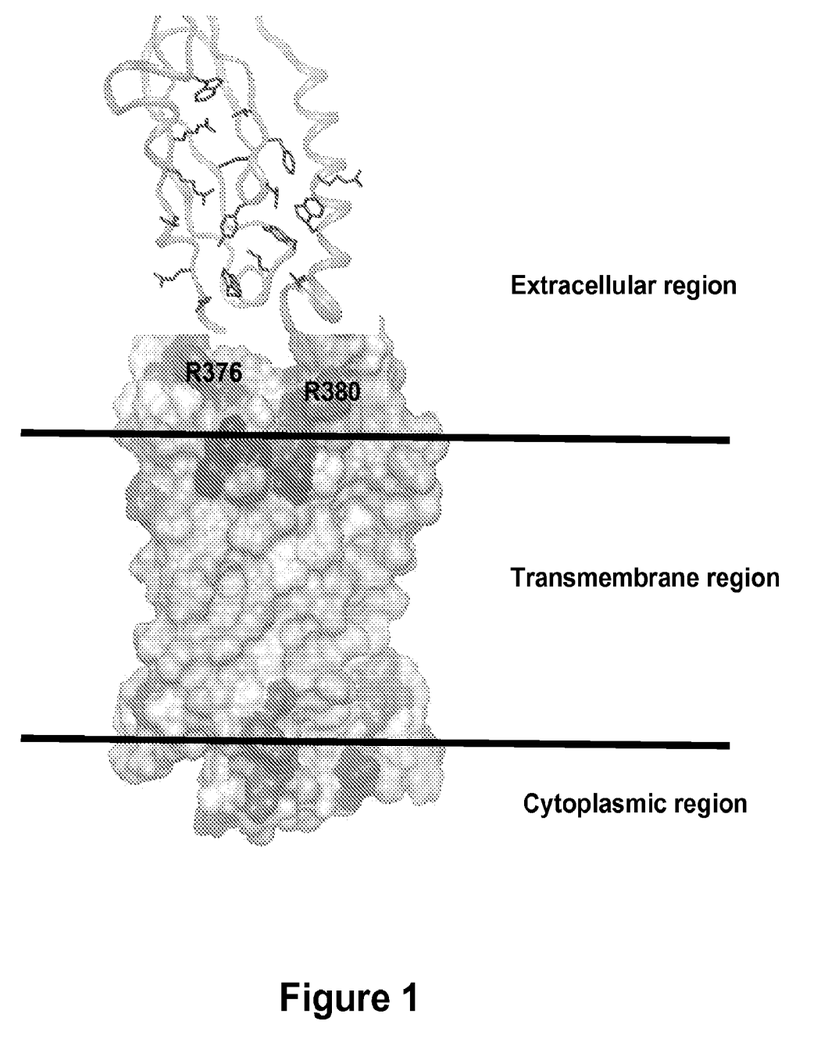
FIG. 1 shows a homology model for the GLP-1R sequence (Primary accession number P43220) constructed using bovine rhodopsin (PDB code: 1F88) and extracellular domain structure of GIP-1R (PDB code: 2qkh) as a template. This model includes an extracellular domain, transmembrane, and intracellular domains.

A homology model for the GLP-1R receptor sequence (Primary accession number P43220) was constructed using bovine rhodopsin (PDB code: 1F88) and extracellular domain structure of the GIP-1R (PDB code: 2qkh) as a template. This model may include a large extracellular domain, a transmembrane domain, and an intracellular domain as shown in FIG. 1. The transmembrane domain consists of seven helices with a hydrophobic "exterior" in contact with the membrane lipid bilayer. The intracellular domain consists of three loops and the C-terminus. Similar models were constructed for mouse(O35659), rat (P32301), chicken (NP_001094505), chimpanzee (XP_527380), dog (XP_538899) GLP-1R sequences.

Two putative binding sites (Site 1 and Site 2) on the extracellular portion of

Figure 3A:
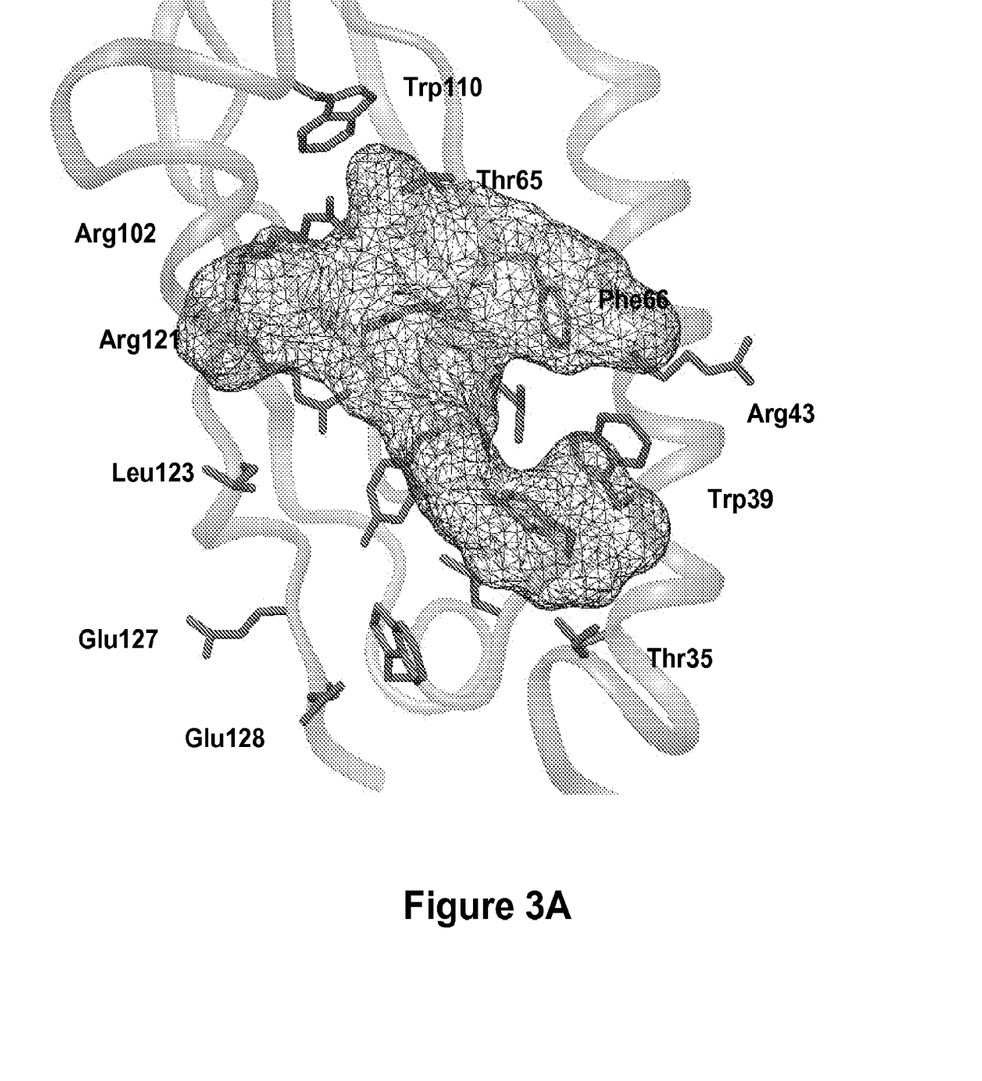
FIGS. 3A and 3B show possible ligand binding modes within the Sites 1 and 2 of FIG. 2A and 2B.
Figure 3B:
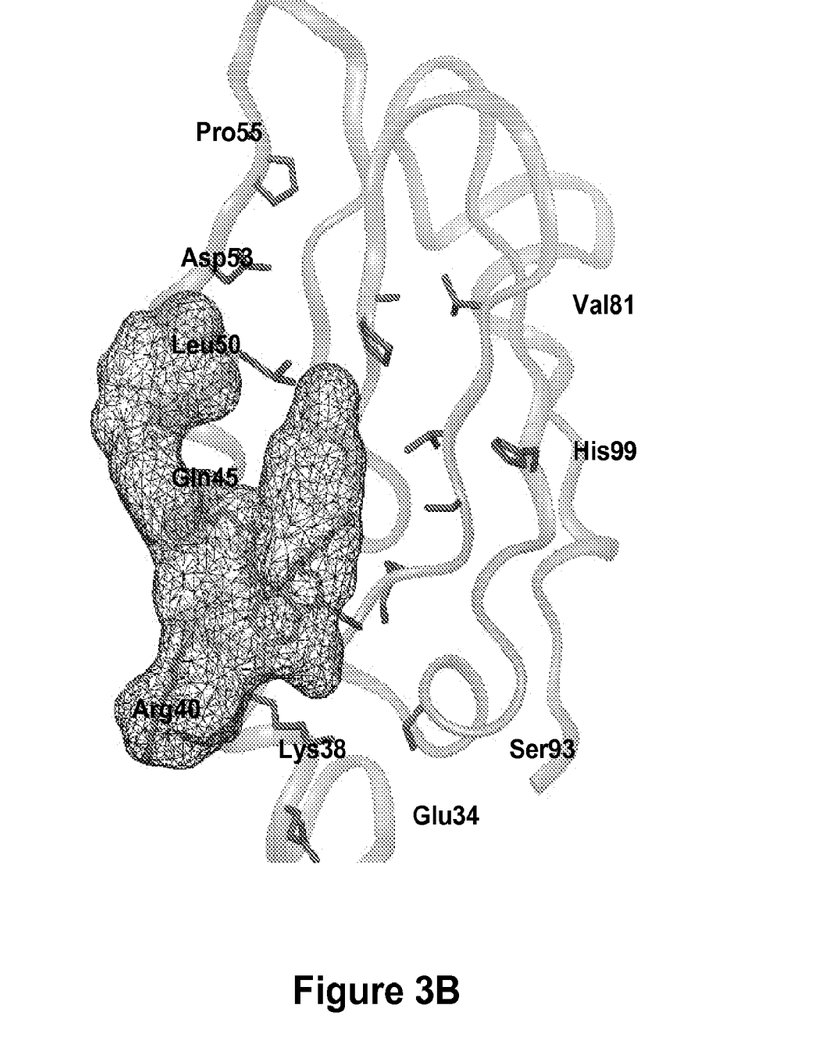

GLP-1R were identified as shown in FIGS. 2A and 2B. Comparing the experimentally determined binding affinities of small molecules with their computed binding scores for Sites 1 and 2, Site 1 was identified as the main ligand binding site. However, Site 2 also has features for binding to small molecule modulators. Site 2 may recognize allosteric-type modulators. FIGS. 3A and 3B show possible ligand binding modes within Site 1 and Site 2.

Site 1 may be defined by eighteen residues: Ser31, Thr35, Trp39, Arg43, Thr65, Phe66, Glu68, Asp67, Tyr69, Trp91, Leu89, Tyr88, Arg121, Arg102, Leu123, Glu127, Trp110 and Glu128. These comprise several hydrophobic, polar, negatively, and positively charged residues.

Site 2 may be defined by seventeen residues: Lys38, Glu34, Trp87, Gln45, Ser49, Asp53, Pro55, Pro73, Val 83, Arg40, Tyr42, Leu50, Ser93, Pro86, His99, Val81 and Ser84.

The identification of Site 1 as the main ligand binding site is consistent with the results of site-directed mutagenesis experiments that suggest that several of the binding site residues listed in the previous paragraph may be critical for the binding of GLP-1 and Exendin-4 to the GLP-1R.

Lead optimization was pursued by novel computational methods to the parent leads (shown in mesh in FIGS. 3A and 3B) followed by suggested structural alterations based on their observed binding environments shown in FIGS. 2A, 2B, 3A and 3B.

The threading approach may reveal distantly homologous proteins that share the same folding structure, but that do not comprise a high amount of sequence similarity. Rather than relying only on sequence alignment, the fold recognition method may blend the sequence-to-structure fitness with other structural characteristics, such as sequence similarity and predicted secondary structures, to find conserved residues that appear in both the template protein of interest (e.g., GLP-1R) as well as any query sequences, and overlay both sequences, maintaining alignment of the conserved residues. Next, the threading program may match the query sequence on the three-dimensional structure of the template using conserved residues of the query protein as the hang points. The resulting model may then be cleaned-up using standard energy minimization and molecular dynamics techniques.

The model may be further refined once the initial structural coordinates are defined. Thus, specific aspects of the model, such as the ligand binding site, may be refined to incorporate the structures of ligands that may be bound at that site.

The structure of the GLP-1R, or a portion thereof, may be defined by the atomic coordinates in three dimensional space. A data set of structural coordinates may define the three dimensional structure of a molecule or molecules. Structural coordinates can be slightly modified and still render nearly identical three dimensional structures. A measure of a unique set of structural coordinates is the root-mean-square deviation of the resulting structure. In alternate embodiments, structural coordinates that render three dimensional structures that deviate from one another by a root-mean-square deviation of less than 3.0 angstroms, or less than 2.0 angstroms, or less than 0.5 angstroms, or less than 0.3 angstroms, may be viewed by a person of ordinary skill in the art as identical or equivalent.

In Silico Screening Of Putative GLP-1R Modulators

The present invention further provides methods to dock compounds of interest, such as putative therapeutic agents, into the structure of the modeled protein to determine whether such putative therapeutic agents may interact with the protein. In one embodiment, the protein of interest is the GLP-1R, and the putative therapeutic agents are putative modulator compounds. Thus, the putative therapeutic agents may bind to the ligand binding site to modify activity of the GLP-1R.

To generate a three dimensional model of a potential modulator compound of interest, or a plurality of potential modulator compounds, a database of in silico structures for potential modulator compounds of interest, such as provided by TTProbes®, may be used. Once the three-dimensional structures of the modulator compounds of interest have been generated, the compounds may be docked into the ligand binding site of the protein of interest.

The putative therapeutic agents (i.e., potential modulator compounds) may comprise a variety of compounds. In one embodiment, the putative therapeutic agent may comprise a peptide or a peptidomimetic. Or, the putative therapeutic agent may comprise an antibody. Alternatively, the putative therapeutic agent may comprise a small organic compound.

The structure of a putative ligand may be provided as a three-dimensional space-filling model, as a rotatable model on a computer screen, or as atomic coordinates in three-dimensional space. In one embodiment, the compounds that dock into the ligand binding site with a negative free energy are considered to be favorable. In alternative embodiments, a compound having an free energy of interaction with the GLP-1R (or another molecule of interest) of less than −2 kcal/mol, or less than −5 kcal/mol, or less than −10 kcal/mole, are considered to provide favorable binding to the protein of interest.

The duration of GLP-1R activation by a putative GLP-1R modulator (hereinafter, "the modulator compound") was studied in HEK293 cells expressing human GLP-1R to assess the effect of the modulator compound on GLP-1R desensitization. In this particular experiment, the maximum amount of cAMP production induced by the modulator compound was about ~80% relative to the maximum amount of cAMP production induced by GLP-1. To assess receptor desensitization, cells were treated with the modulator compound or GLP-1 for 30 minutes. The cells were then washed and incubated for an additional 30 minutes in the absence of ligand and/or modulator compound. The amount of cAMP produced was then quantified. Interestingly, cAMP production is sustained (90%) following removal of the modulator compound or GLP-1. However, unlike cells treated with GLP-1 initially, cells treated with the modulator compound followed by further addition of the modulator compound or GLP-1 were further stimulated suggesting that the GLP-1R was not desensitized by the modulator compound to the same extent that it was by the native ligand. In conclusion, activation of the GLP-1R by the modulator compound is prolonged and the GLP-1R can be re-stimulated with GLP-1 peptide, illustrating that the modulator compound does not down-regulate the human GLP-1R function in HEK293 cells expressing the human GLP-1R. This may allow for a prolonged efficacy of in vivo with the modulator compound when compared to native ligand.

In order to confirm that the apparent GLP-1R modulation seen in the cell-based assay was specific, a modulator compound was evaluated in an in vitro receptor-binding assay. This assay was designed as a competition assay where the modulator compound was evaluated for its ability to inhibit $^{125}$I labeled human GLP-1 (7-36) from binding to membrane preparations derived from cells expressing the human or mouse GLP-1R. The modulator compound effectively inhibited binding of $^{125}$I GLP-1 (7-36) to the human or mouse GLP-1R with $EC_{50}$ values of 236 nM and 188 nM, respectively. These data suggest that the modulator compound binds to the GLP-1R derived from human or mouse cells with comparable efficiency; however, functionally it stimulates the human receptor to a greater degree than the mouse and rat receptors.

To determine whether the binding of the modulator compound to GLP-1R is competitive with respect to the binding of the GLP-1 peptide, the modulator compound's binding was studied in the presence of varying concentrations of $^{125}$I-labeled human GLP-1 (7-36). Increasing the concentrations of $^{125}$I-labeled human GLP-1 (7-36) did not change the modulator compound's potency for inhibition of $^{125}$I-labeled human GLP-1 (7-36) binding to membranes. This data suggests the binding of the modulator compound to GLP-1R is non-competitive with respect to the binding of GLP-1 (7-36). Finally, the selectivity of the GLP-1R for the modulator compound was further tested against the GLP-1, GIP and the Glucagon Receptors in a cAMP functional cell-based assay. The modulator compound did not stimulate activation of the GIP and Glucagon Receptor's cAMP production at concentrations up to 100 µM. In addition, the modulator compound did not block glucagon receptor function in the presence of glucagon peptide (data not shown).

The modulator compound may be any compound known to modulate the activity of the GLP-1R. In one embodiment, the modulator compound may be a compound known to be an agonist of the GLP-1R. In another embodiment, the modulator compound may be a compound as identified in U.S. Provisional Patent applications 61/034,599 and 61/034,606, both disclosures of which are herein incorporated by reference.

Figure 4:
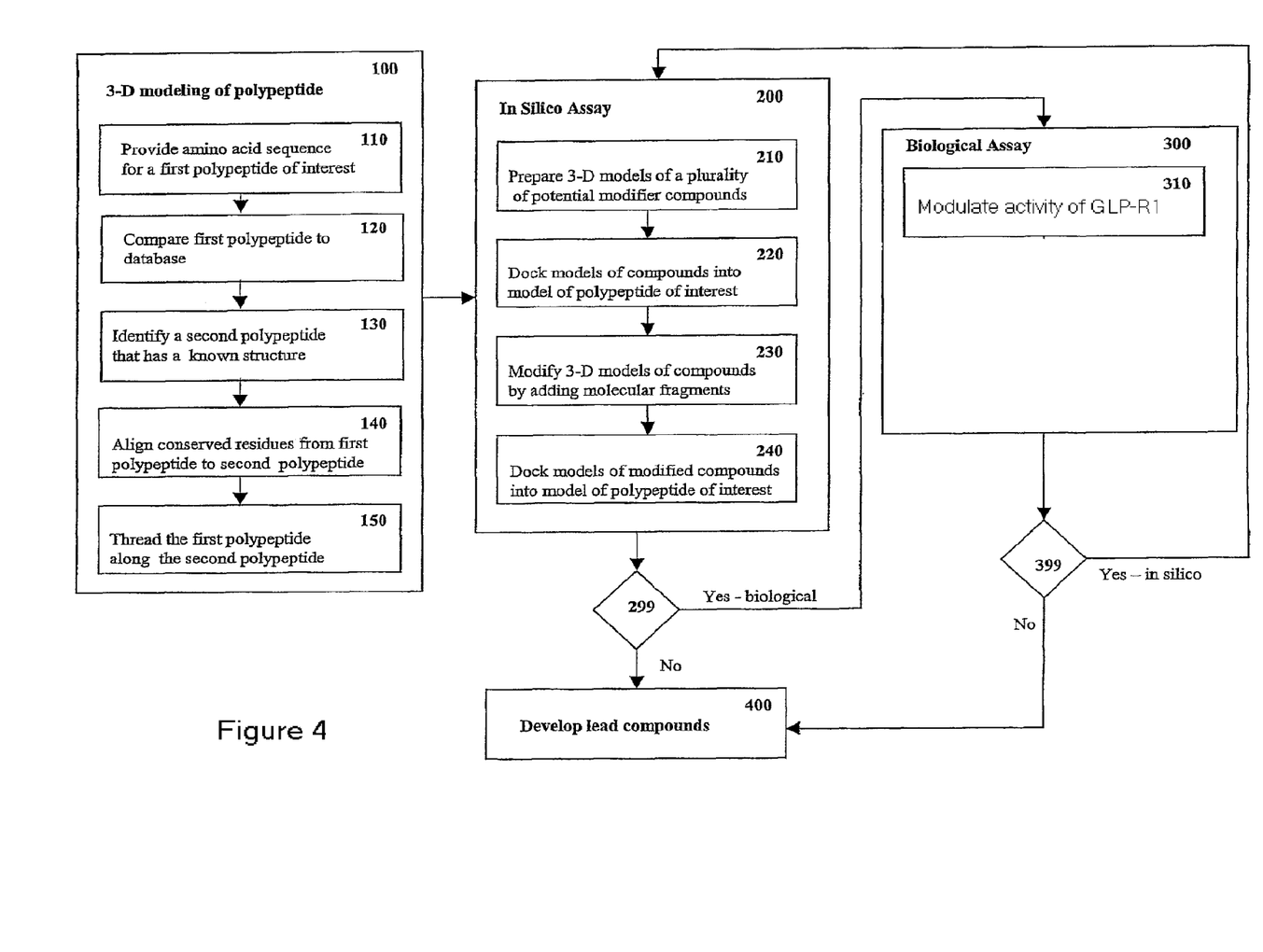
FIG. 4 shows a schematic of a method used to develop modulators of a target receptor.

A schematic of a method used to develop modulators of the GLP-1R is shown in FIG. 4. Thus, the method may include a first stage 100 of developing a three-dimensional model of a protein or polypeptide of interest (e.g., the GLP-1R). As described herein, the method may comprise providing the amino acid sequence for the protein or polypeptide of interest 110. The sequence of the protein or polypeptide of interest may then be compared to amino acid sequences available in protein sequence databases 120 to identify proteins or polypeptides that have a known structure, and that may be homologous in structure to the protein or polypeptide of interest 130. If a second polypeptide or protein of known structure that has a sequence that includes regions of identity to the protein or polypeptide of interest is identified, the second protein may be used to align conserved residues from the second protein or polypeptide with the first protein or polypeptide of interest 140. The aligned residues (hang-points) may then be used as anchors as the first polypeptide or protein of interest is threaded along the structure of the second protein or polypeptide of interest to construct a three-dimensional model of the first polypeptide or protein of interest 150.

Once a three-dimensional model of the protein or polypeptide of interest has been constructed, it may be used in an in silico assay for screening a plurality of compounds 200. The in silico assay may comprise generating a library of three-dimensional structures for potential therapeutic agents 210. For example, in one embodiment a library of small high information density organic molecules (i.e., a library, wherein each small molecule within the library contains at least one functional group of interest) may be prepared. Such a library is provided by TTProbes® (TransTech Pharma., Inc., High Point, N.C.) which is a set of more than 51,000 pharmacophorically diverse molecules of high information density. The in silico probes may then be docked with the three-dimensional structure of the protein or polypeptide of interest as described herein to determine the atomic interactions between the protein/polypeptide and the compound 220. Optionally, the compound may also be modified by adding or removing molecular fragments from the compound 230, and then the modified compounds docked into the three-dimensional structure of the protein or polypeptide of interest 240 to determine how the changes to the structure of the compound may affect the interaction of the compound with the protein/polypeptide. Such molecular alterations may be made until there is no longer an apparent improvement in the ability of the compound to interact with the polypeptide/protein of interest. For example, for GLP-1R, and using the TTProbes® in silico library, over 3,000 candidate potential GLP-1R modulators were identified. The method may include the option 299 of developing the compounds identified by in silico screening or performing further testing of the compounds by a biological assay.

Thus, still referring to FIG. 4, the putative therapeutic agents (i.e., potential modulator compounds) identified by in silico screening may then be evaluated by other types of assays for biological activity 300. For example, a putative receptor ligand may be evaluated using a binding assay. For modulators of GLP-1R, the compounds may be evaluated to determine whether they modulate the activity of the GLP-1R 310.

The results of the biological testing may indicate that certain structures are of interest as displaying efficacy as modulators of GLP-1R activity. Thus, there is the option 399 to test at least some of these structures in additional in silico assays to determine if additional chemical modifications may be made to the structures to improve the therapeutic effects. Alternatively, the compounds may be considered as optimized and, thus, comprise lead compounds for additional animal studies and the like 400.

Therapeutics

The invention further provides pharmaceutical compositions comprising the modulator compounds of the invention. The pharmaceutical compositions containing a compound of the invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

They may also be coated by the techniques described in U.S. Pat. Nos. 4,356,108; 4,166,452; and 4,265,874, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example, peanut oil, liquid paraffin, or olive oil.

Aqueous suspensions may contain the active compounds in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more coloring agents, one or more flavoring agents, and one or more sweetening agents, such as sucrose or saccharin.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of said partial esters with ethylene oxide, for example polyoxyethylene sorbitan monooleate. The emulsions may also contain sweetening and flavoring agents.

Also, oily suspensions may be formulated by suspending the active ingredient in a vegetable oil, for example, arachis oil, olive oil, sesame oil or coconut oil, or in a mineral oil such as a liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may also be in the form of a sterile injectible aqueous or oleaginous suspension. This suspension may be formulated according to the known methods using suitable dispersing or wetting agents and suspending agents as described above. The sterile injectible preparation may also be a sterile injectible solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland, fixed oil may be employed using synthetic mono- or diglycerides. In addition, fatty acids such as oleic acid find use in the preparation of injectibles.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, as, for example, for treatment of molluscipox virus, creams, ointments, jellies, solutions of suspensions, etc., containing the compounds of the invention are contemplated. For the purpose of this application, topical applications shall include mouthwashes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Pharmaceutically acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Methanesulfonate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, of the compounds of the present invention, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, male ate, private, malamute, succinct, citrate, tartarate, fumarate, mandelate, benzoate, cinnamate, methanesulfonate, ethanesulfonate, picrate and the like. Other salts, which are not pharmaceutically acceptable, may be useful in the preparation of compounds of the invention; these form a further aspect of the invention.

Thus, in another embodiment of the present invention, there is provided a pharmaceutical composition comprising a therapeutically effective amount of a compound identified as binding to or modulating the GLP-1R, or a pharmaceutically acceptable salt thereof, and one or more pharmaceutically acceptable carriers, excipients, or diluents. In an embodiment of the pharmaceutical composition, the compound identified as binding to or modulating the GLP-1R is an agonist of the human GLP-1R.

In another embodiment, the present invention provides a pharmaceutical composition comprising a therapeutically effective amount of the compound identified as binding to or modulating the GLP-1R, and one or more pharmaceutically acceptable carriers, excipients, or diluents.

In another embodiment, the present invention provides a pharmaceutical composition comprising a therapeutically effective amount of the compound identified as binding to, or modulating the GLP-1R, and one or more pharmaceutically acceptable carriers, excipients, or diluents, and further comprising one or more additional therapeutic agents.

The compound identified as binding to, or modulating the GLP-1R, may be administered in an amount sufficient to modulate GLP-1R activity in a subject. The compound identified as binding to or modulating the GLP-1R may be administered in the form of an oral dosage or parenteral dosage unit. In alternative embodiments, the compound identified as binding to, or modulating the GLP-1R, is administered as a dose in a range from about 0.01 to 1,000 mg/kg of body weight per day, or as a dose in a range from about 0.1 to 100 mg/kg of body weight per day, or as a dose in a range from about 0.5 to 10 mg/kg of body weight per day.

EXAMPLES

Example 1

Materials and Methods

Small organic compound stocks may be prepared as described in U.S. Provisional Patent applications 61/034,599 and 61/034,606.

Example 2

Computer Modeling

TransTech Pharma's Translational Technology™, described in U.S. Patent Publications 2003/0125315, 2004/0019432 and 2004/0010515, each of which are incorporated by reference in their entireties, may be used to model the GLP-1R domain, to discover specific small molecule inhibitors, and to optimize GLP-1R binding agents into preclinical drug candidates. TransTech Pharma's Translational Technology™ was designed and developed for rapid lead generation and optimization of drug candidates. The system consists of two subtechnologies: TTProbes™ and TTPredict™. TTProbes™ is a set of greater than 51,000 pharmacologically diverse molecules. TTPredict™ is a computer-based technology that automates high-throughput three-dimensional target model building, binding site identification, and conformational analysis. The TTPredict computer program is used to dock, score, and rank members of TTProbes set with a target binding site.

To develop putative modulator compounds, TTPredict™ was used to construct threading and homology models for the GLP-1R.

Example 3

In Silico Assay

TTProbes molecules may be docked into the putative ligand binding site of GLP-1R (FIGS. 2A and 2B). The fit of every docked TTProbes molecule may be computed using several scoring functions. High-scoring molecules may be identified, and the highest ranking TTProbes molecules may be submitted for in vivo screening.

For the GLP-1R, the amino acid residues Ser31, Thr35, Trp39, Arg43, Thr65, Phe66, Glu68, Asp67, Tyr69, Trp91, Leu89, Tyr88, Arg121, Arg102, Leu123, Glu127, Trp110 and Glu128 are predicted to be important in binding to substrates within Site 1, as described above. In addition, residues: Lys38, Glu34, Trp87, Gln45, Ser49, Asp53, Pro55, Pro73, Val 83, Arg40, Tyr42, Leu50, Ser93, Pro86, His99, Val81 and Ser84 are predicted to be important in binding to substrates within Site 2, as described above.

The 51,389 probe molecules comprising TTProbes™ database may be docked into the binding site. The fit of every docked TTProbes molecule may be computed using several scoring functions. Prior to docking the TTProbes molecules into the GLP-1R active site, 1000 low energy conformers per molecule may be generated using Monte-Carlo procedures. TTPredict™ may be used to dock in silico every conformer with the predicted site (e.g., Site 1 and Site 2) of the GLP-1R.

Individual or consensus scoring functions including LUDI (Böohm, H. J., 1994, *J. Comp. Aided Molec. Design,* 8:243-256), PLP (Gehlhaar et al, 1995, *Chem. Bio.,* 2:317-324), DOCK (Meng, E. C., et al., 1992, *J. Comp. Chem.* 13:505-524), LigFit, (Accelrys, San Diego, Calif.), JAIN (Jain, A. N., 1996, *J. Comp. Aided Molec. Design* 10:427-440), and Poisson-Boltzmann (Honig, B. et al., 1995, *Science,* 268:1144-9) may be used. High consensus scoring TTProbes molecules may be identified and the highest-ranking probes may be submitted for in vitro (i.e., biological) testing.

Biological Assay

The following assay methods may be utilized to identify compounds that are effective in showing modulation of the GLP-1R.

Receptor Binding Assay

The affinity of compounds for GLP-1 receptor may be studied in an [$^{125}$I]GLP-1(aa 7-36) equilibrium radioligand binding assay. Membranes from CHO cells expressing the human GLP-1R may be used in the GLP-1R binding assay. Reactions may be carried out in 96-well plates. Compound may be diluted in 20% DMSO/water. A final binding assay concentration of the compound ranging from 0.1 nM to 100 uM in 2% DMSO concentration may be used. The final binding assay conditions may be 25 mM Tris-HCL, pH 7.4 buffer containing 10 mM $MgCl_2$, 1 mM DTT, 0.1 mM EDTA, 0.1 mM EGTA, 0.1% BSA, 1-10 ug membrane, 20-200 pM [$^{125}$I] GLP-1 (aa 7-36) (SA=2200 Ci/mmoL), (Perkin Elmer part no. NEX308), and compound in final DMSO concentration of 2% (final assay volume of 100 uL). Positive control wells (C+) may lack compound, and negative control wells (C-) may lack compound and may contain excess non-radio-labeled GLP-1 (1 μM). Non-specific binding (NSB) may be determined for each compound concentration by addition of cold excess GLP-1 (1 μM). The reaction may be carried out at room temp for 120 min. Membranes containing bound [$^{125}$I] GLP-1 (aa 7-36) ligand may be isolated following filtration onto Unifilter-96 GF/C filter plates (PerkinElmer part no. 6005177) using a cell harvester instrument. Plates may be washed 5 times with cold 25 mM Tris-HCL, pH 7.5 containing 0.05% bovine serum albumin (BSA). Following filtration, 50 μL of Microscint PS (Packard part no. 6013631) may be added and plates may be sealed with TopSeal-A adhesive seals (Packard part no. 6005185). $^{125}$I isotope bound to the Unifilter-96 GF/C plates may be counted using a TopCount instrument (Packard).

Percent inhibition of [$^{125}$I] GLP-1 (aa 7-36) binding may be calculated according to the equation $100\times1-\{(Sample_{cpm}-NSB_{cpm})/C+_{cpm}-C-_{cpm})\}$. Percent inhibition of [$^{125}$I]GLP-1 binding (Y) vs compound concentration (X) data may be generated. The $IC_{50}$ values may be calculated by fitting the data using parameters for a sigmoidal dose response, variable slope nonlinear regression (GraphPAD Prizm, San Diego, Calif.) according to the equation:

$$Y = Bottom + (Top-Bottom)/(1+10^{((Log\ EC50-X)*HillSlope)})$$

X is the logarithm of concentration. Y is the response. Y starts at Bottom and goes to Top with a sigmoid shape.

Functional Cell-based Assay

The efficacy of GLP-1R agonists may be studied in a cAMP production functional assay using HEK-293 cells expressing the cloned human GLP-1R. GLP-1R-expressing cells (10,000 cells per 0.1 mL) may be plated in 96-well plates in Dulbecco's Modified Eagles Media (DMEM) containing 10% fetal bovine serum and penicillin-streptomycin. Following overnight incubation of cells, media may be removed, and compounds (at concentrations ranging from 0.0001 to 100 μM) may be added to monolayer cells in Iscove's Modified Dulbecco's Medium (IMDM), 100 μM RO 20-1724 PDE inhibitor, 0.1% BSA, 2% DMSO in a final volume of 100 μL, and incubated for 30 min at 37° C. 95% $O_2$, 5% $CO_2$ in a humidified incubator. cAMP production may be quantitated using a homogenous time-resolved fluorescence detection system (cAMP Dynamic, CIS bio International). GLP-1 may typically produce cAMP production dose response curves with $EC_{50}$ values ranging from about 0.01 μM-100 μM, typically ranging from about 0.02 μM to about 10 μM. Receptor activation may be expressed as percentage relative to maximal GLP-1-induced cAMP accumulation. Percent GLP-1 activation vs compound concentration dose response curves may be generated by fitting the data using a sigmoidal dose response curve-fitting program (GraphPAD Prizm). Several compounds may exhibit an EC-50 from about 20 nM to about 500 nM with GLP-1R activation ranging from about 32% to about 64%.

The specificity of GLP-1 agonists for the GLP-1R may be confirmed by performing the assay with vector-control mock cells which lack the cloned human GLP-1R. All compounds may be devoid of cAMP accumulation in the mock-transfected cell lines.

While the invention has been described and illustrated with reference to certain preferred embodiments thereof, those skilled in the art will appreciate that various changes, modifications and substitutions can be made therein without departing from the spirit and scope of the invention.

What is claimed is:

1. A method for identifying a compound having the ability to modulate the GLP-1 receptor (GLP-1R), the method comprising the steps of:

generating a first three-dimensional model of the GLP-1R;

generating a second three-dimensional model of a potential modulator compound;

using a computer to dock the second three-dimensional model with the first three-dimensional model; and quantifying at least one atomic interaction between the potential modulator compound and the GLP-1R, or a portion thereof, wherein the first three-dimensional model is a computer model of the GLP-1R, wherein the computer model comprises extracellular, transmembrane, and intracellular domains of GLP-1R;

the second three-dimensional model is a computer model of the potential modulator compound and the potential modulator compound has a molecular weight of less than 2,000 daltons;

the atomic interaction between the potential modulator compound and the GLP-1R does not interfere with the binding of native GLP-1 to the GLP-1R;

the atomic interaction between the potential modulator compound and the GLP-1R comprises at least one atomic interaction between the potential modulator compound and at least one of the amino acid residues selected from the group consisting of Ser31, Thr35, Trp39, Arg43, Thr65, Phe66, Glu68, Asp67, Tyr69, Trp91, Leu89, Tyr88, Arg121, Arg102, Leu123, Glu127, Trp110 and Glu128 of the GLP-1R; and the atomic interaction between the potential modulator compound and the GLP-1R comprises at least one atomic interaction between the potential modulator compound and at least one of the amino acid residues selected from the group consisting of Arg376 and Arg380.

2. The method of claim 1, further comprising:
modifying the computer model of the potential modulator compound; and
evaluating how modifying the computer model of the potential modulator compound changes at least one atomic interaction between the first three-dimensional model and the second three-dimensional model.

3. The method of claim 2, wherein the step of modifying the computer model of the potential modulator compound comprises:
searching a library of molecular structures for molecular fragments that can be linked to the potential modulator compound, wherein a molecular fragment comprises at least one atom; and
linking a fragment to the potential modulator compound to generate a modified computer model of the compound.

4. The method of claim 1, wherein the atomic interaction between a potential modulator compound and the GLP-1R, or a portion thereof, comprises at least one atomic interaction selected from the group consisting of charge, electrostatic, hydrogen bond and hydrophobic.

5. The method of claim 1, wherein the atomic interaction between a potential modulator compound and the GLP-1R, or a portion thereof, comprises at least two hydrogen bond atomic interactions, at least two hydrophobic atomic interactions and at least one of a charge or electrostatic atomic interaction.

6. The method of claim 1, wherein the atomic interaction between a potential modulator compound and the GLP-1R, or a portion thereof, comprises at least three hydrogen bond atomic interactions, at least three hydrophobic atomic interactions and at least one of a charge or electrostatic atomic interaction.

* * * * *